United States Patent [19]

Kocses

[11] Patent Number: 5,026,354
[45] Date of Patent: Jun. 25, 1991

[54] SAFETY SYRINGE APPARATUS

[76] Inventor: Joseph W. Kocses, 117 Rochelle Pkwy., Saddle Brook, N.J. 07662

[21] Appl. No.: 541,324

[22] Filed: Jun. 21, 1990

[51] Int. Cl.$^5$ .............................................. A61M 5/32
[52] U.S. Cl. .................................. 604/195; 604/110; 604/220
[58] Field of Search ............... 604/195, 198, 110, 263, 604/218, 187, 220

[56] References Cited

U.S. PATENT DOCUMENTS

| | | | |
|---|---|---|---|
| 4,233,975 | 11/1980 | Yerman | 604/110 |
| 4,747,837 | 5/1988 | Hauck | 604/198 |
| 4,846,796 | 7/1989 | Carrell et al. | 604/110 |
| 4,850,968 | 7/1989 | Romano | 604/218 X |
| 4,921,486 | 5/1990 | Dechellis et al. | 604/195 X |
| 4,947,863 | 8/1990 | Haber et al. | 604/263 X |

Primary Examiner—John D. Yasko
Attorney, Agent, or Firm—Leon Gilden

[57] ABSTRACT

An apparatus to prevent spread of transmittable diseases, including a syringe defined by a cylindrical barrel containing a reciprocatable plunger therewithin. The plunger is provided with mechanical communication to a needle chamber mounted within a needle body of the barrel. Subsequent to filling and usage of the cavity defined within the barrel, the plunger is retracted to space a lower locking skirt above an upper locking skirt, wherein the locking skirts are arranged to prevent projection of the plunger back into the barrel, and wherein the plunger by mechanical connection to the needle chamber retracts the needle interiorly of the barrel preventing its reuse.

4 Claims, 3 Drawing Sheets

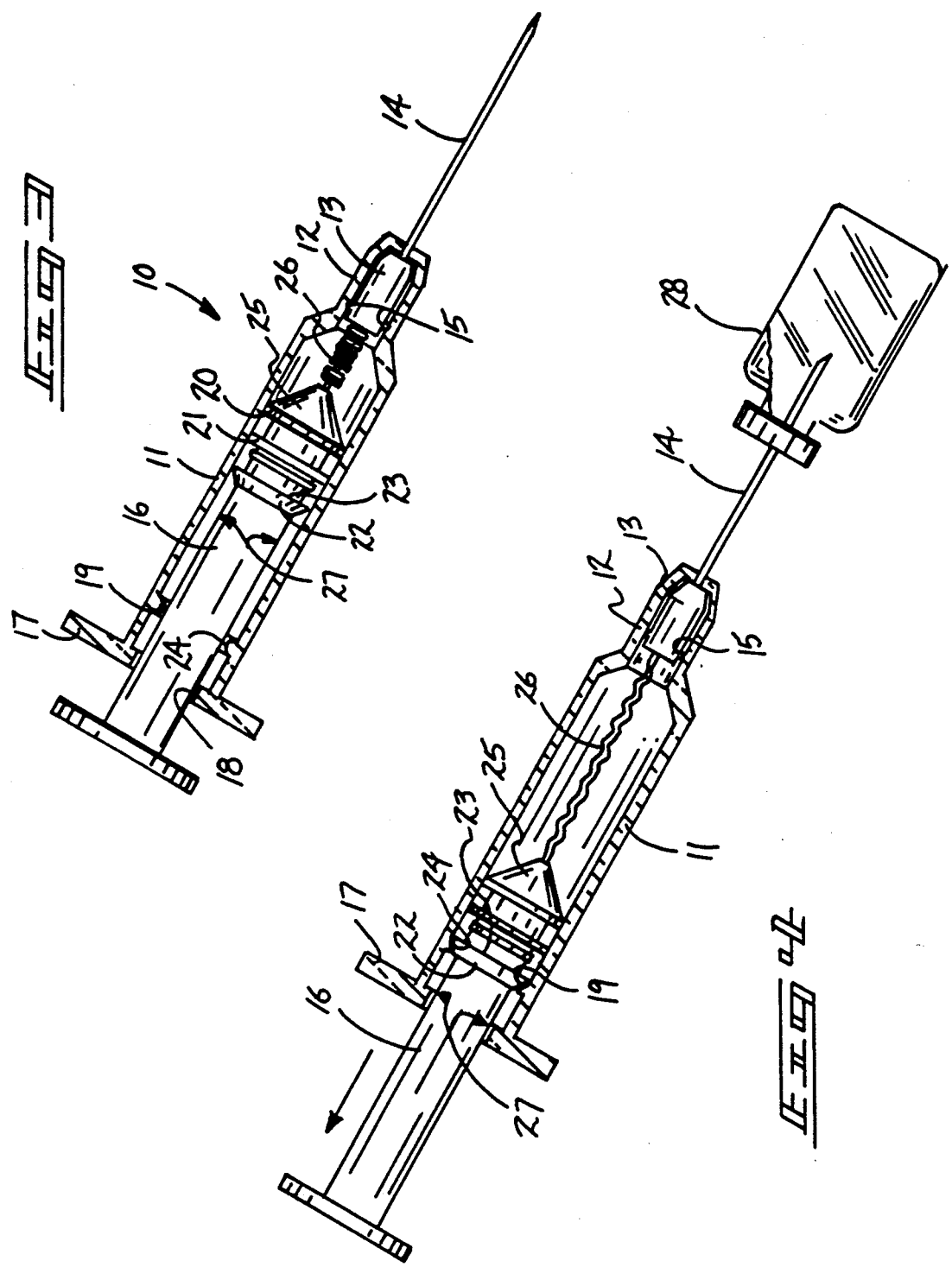

5,026,354

SAFETY SYRINGE APPARATUS

BACKGROUND OF THE INVENTION

1. Field of the Invention

The field of invention relates to syringe construction, and more particularly pertains to a new and improved safety syringe apparatus wherein the same is arranged to prevent reuse of a syringe organization to minimize spread of transmittable disease.

2. Description of the Prior Art

Contemporary society is experiencing an alarming spread of transmittable disease, and particularly disease such as AIDS, wherein the disease is notoriously conspicuous among drug addicts utilizing a syringe in a multiple of applications thereby spreading the disease. Further, the use of the instant invention prevents reuse of the needle portion of the organization further preventing spread of bacteriological and viral infections. Prior art hypodermic needle organizations are utilized in the prior art and may be found for example in U.S. Pat. No. 4,687,467 wherein the piston of the plunger is destroyed upon forward projection of the plunger in its use.

U.S. Pat. No. 4,781,683 to Woznika sets forth a single use syringe organization wherein an expansion plug positioned in the outlet flow channel of the syringe expands after being exposed to a drug containing water.

U.S Pat. No. 4,207,870 to Eldridge sets forth a syringe organization utilizing a one-way valve positioned within a chamber allowing the venting of air as blood enters the chamber, but is not allowed the passage of blood.

U S. Pat. No. 4,775,364 to Alles sets forth a nonreusable syringe organization wherein the plunger includes a lip when projected forwardly rides over an associated cooperating lip preventing retraction of the plunger relative to the syringe body.

U.S Pat. No. 4,226,236 to Genese sets forth a multi-compartment syringe arranged for expelling of the medicant in the syringe as the plunger is directed through the body of the syringe effecting mixing of the medication contained therewithin.

As such, it may be appreciated that there continues to be a need for a new and improved safety syringe apparatus wherein the same addresses both the problems of ease of use as well as effectiveness in construction in preventing reuse of the organization subsequent to injection within an individual and in this respect, the present invention substantially fulfills this need.

SUMMARY OF THE INVENTION

In view of the foregoing disadvantages inherent in the known types of syringe apparatus now present in the prior art, the present invention provides a safety syringe apparatus wherein the same is arranged to effect locking of the needle portion of the syringe organization interiorly of the syringe body subsequent to use. As such, the general purpose of the present invention, which will be described subsequently in greater detail, is to provide a new and improved safety syringe apparatus which has all the advantages of the prior art syringe apparatus and none of the disadvantages.

To attain this, the present invention provides an apparatus to prevent spread of transmittable diseases, including a syringe defined by a cylindrical barrel containing a reciprocatable plunger therewithin. The plunger is provided with mechanical communication to a needle chamber mounted within a needle body of the barrel. Subsequent to filling and usage of the cavity defined within the barrel, the plunger is retracted to space a lower locking skirt above an upper locking skirt, wherein the locking skirts are arranged to prevent projection of the plunger back into the barrel, and wherein the plunger by mechanical connection to the needle chamber retracts the needle interiorly of the barrel preventing its reuse.

My invention resides not in any one of these features per se. but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved safety syringe apparatus which has all the advantages of the prior art syringe apparatus and none of the disadvantages.

It is another object of the present invention to provide a new and improved safety syringe apparatus which may be easily and efficiently manufactured and marketed.

It is a further object of the present invention to provide a new and improved safety syringe apparatus which is of a durable and reliable construction.

An even further object of the present invention is to provide a new and improved safety syringe apparatus which is susceptible of a low cost of manufacture with regard to both materials and labor, and which accordingly is then susceptible of low prices of sale to the consuming public, thereby making such safety syringe apparatus economically available to the buying public.

Still yet another object of the present invention is to provide a new and improved safety syringe apparatus which provides in the apparatuses and methods of the prior art some of the advantages thereof, while simultaneously overcoming some of the disadvantages normally associated therewith.

Still another object of the present invention is to provide a new and improved safety syringe apparatus wherein the same retracts the tube-like needle within the body of the syringe apparatus subsequent to use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic cross-sectional illustration of the instant invention.

FIG. 4 is an orthographic cross-sectional illustration of the apparatus in a retracted and filling configuration.

DESCRIPTION OF THE PREFERRED EMBODIMENT

Figure 1:
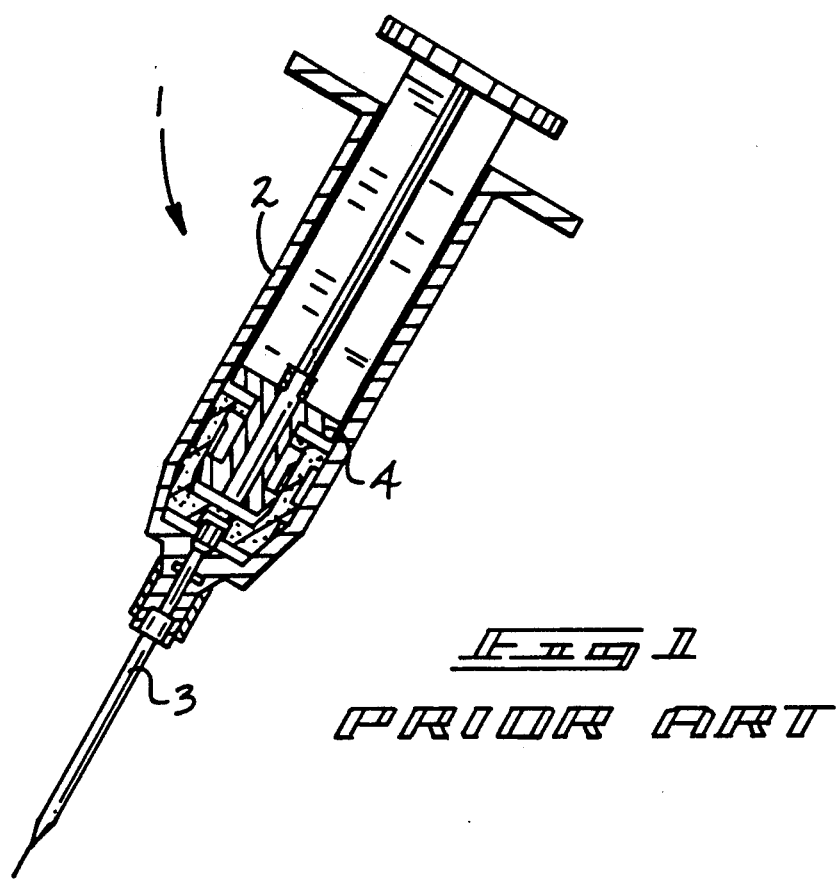
FIG. 1 is an orthographic cross-sectional view of a prior art syringe apparatus.

With reference now to the drawings, and in particular to FIGS. 1 to 6 thereof, a new and improved safety syringe apparatus embodying the principles and concepts of the present invention and generally designated by the reference numeral 10 will be described.

Figure 2:
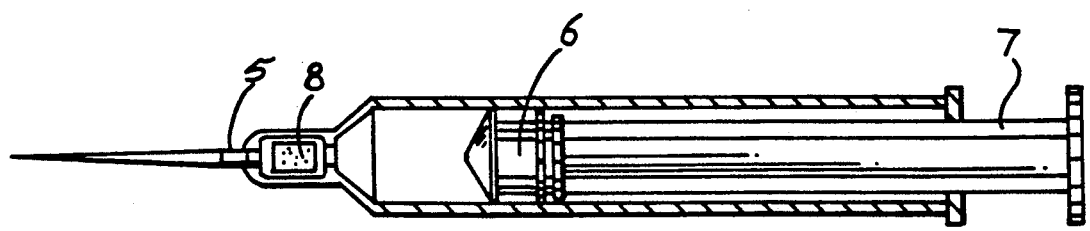
FIG. 2 is an orthographic cross-sectional view of a further prior art syringe organization.

FIG. 1 illustrates a prior art syringe apparatus 1, including a tubular body 2 mounting a syringe needle 3 in its lowermost end, wherein the plunger 4 is severed subsequent to its use by projection of a forward face of the plunger, with a rear face of the needle to effect severing of the plunger, in a manner as set forth in U.S. Pat. No. 4,687,467. FIG. 2 illustrates a further syringe apparatus, wherein the plunger 7 includes a forward piston and in sealing relationship within the housing of the organization, wherein water absorbent member 8 mounted rearwardly of the needle 5 expands subsequent to use when in communication with a fluid such as water to restrict the channel and limit use of the organization to one application.

Figure 5:
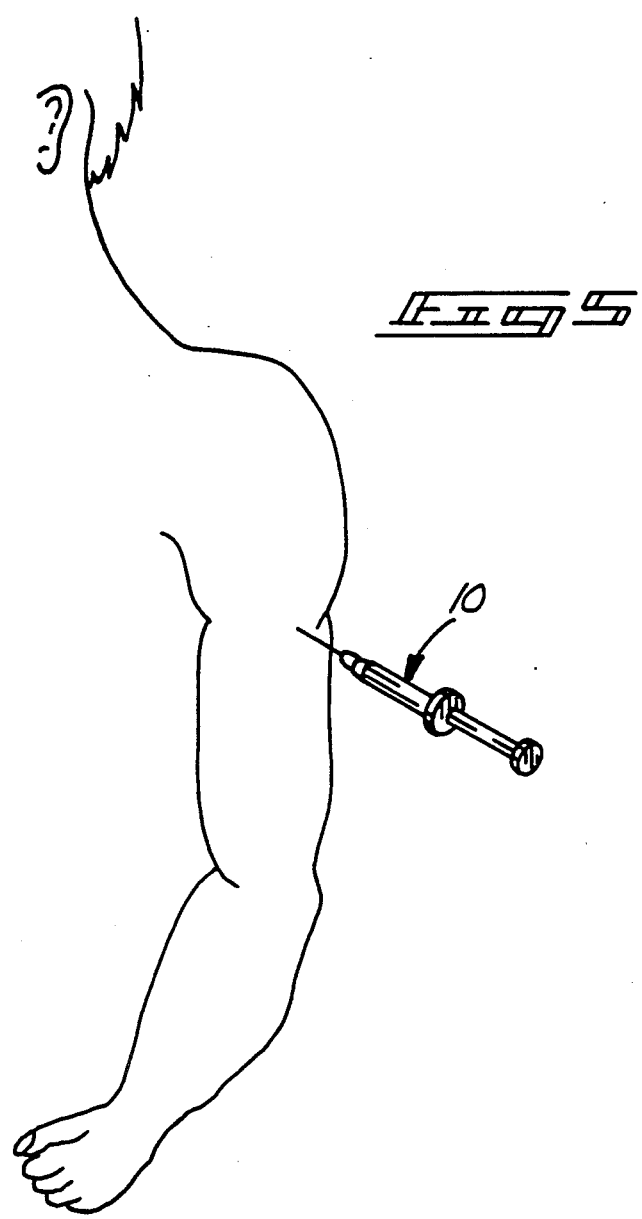
FIG. 5 is an isometric illustration of the syringe apparatus in use.

More specifically, the safety syringe apparatus 10 of the instant invention essentially comprises a cylindrical barrel 11 and a coaxially aligned integral needle body 12 arranged within a forward end of the barrel 11 defining a cavity therewithin of a lesser diameter than that defined by the barrel 11 to encompass a needle chamber 13 that is mounted within the needle body 12, including at least one or a plurality of rib projections 15 received within an annular ribbed recess 29 (see FIG. 6) to position the needle chamber 13 within the needle body 12. The needle chamber 13 is in fluid communication with a tubular needle member 14 coaxially and forwardly directed and integrally formed to the needle chamber 13 and directed forwardly of the needle body 12. The needle chamber 13 further permits fluid flow therethrough to permit communication between an internal cavity defined within the cylindrical barrel 11 positioned forwardly of the associated plunger 16 to directed fluid flow from the so defined cavity through the needle member 14 in a conventional manner to administer injection of a medicine and the like, in a manner as illustrated in FIG. 5. The barrel 11 includes a flange 17 directed orthogonally and outwardly relative to an upper terminal end of the barrel 11, wherein the flange 17 includes a flange opening 18 to slidably receive the plunger 16 therethrough. The barrel 11 includes an upper annular locking skirt integrally formed adjacent the upper terminal end of the barrel 11, wherein the upper annular locking skirt 19 is defined by an upper annular locking edge 24 positioned in a spaced relationship from the interior wall of the barrel 11 adjacent an exterior surface of the plunger 16. The skirt 19 includes a conical surface directed downwardly relative to the upper annular locking edge 24 towards the interior surface of the barrel 11. The plunger 16 has integrally mounted thereto a lower deformable annular locking skirt 22 cooperative with the upper annular locking skirt 19. The lower annular skirt 22 includes a lower annular edge 23, with the annular locking skirt 22 defining a lower conical surface directed upwardly from the edge 23 towards the plunger 16. In this manner, the upper locking skirt 19 defines a top planar annular surface, while the lower skirt 22 defines a lower planar surface, whereupon retraction of the plunger 16 outwardly relative to the barrel 11, retracts indicia 27 beyond and above the flange 17 to indicate simultaneously the directing of the lower locking skirt 22 above the upper locking skirt 19 to effect confronting of the lower annular surface to overlie and confront in contiguous relationship the upper annular surface of the upper locking skirt 19, in a manner as illustrated in FIG. 6 for example.

Upon retraction of the plunger 16 to the second position where the lower locking skirt is spaced above the upper locking skirt from a first position, where the lower locking skirt is spaced below the locking skirt, the plunger 16 is prevented from and directed interiorly of the barrel 11 as the confronting planar annular surfaces of the respective locking surfaces prevent return of the plunger interiorly of the barrel.

Figure 6:
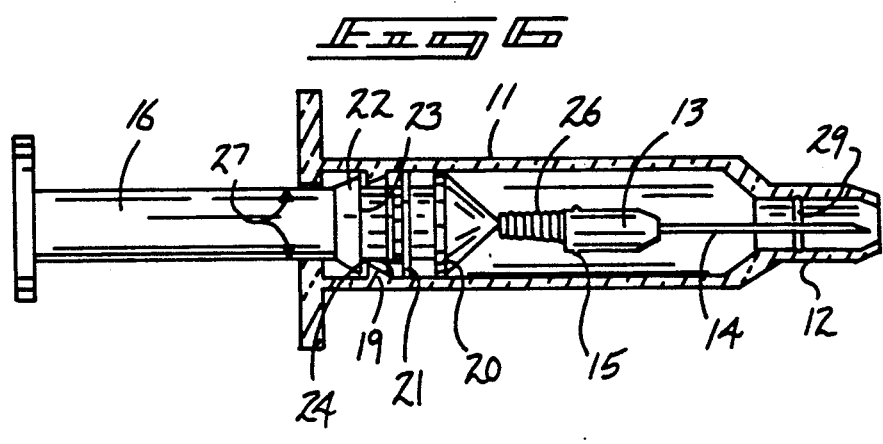
FIG. 6 is an orthographic cross-sectional illustration of the plunger of the apparatus in a retracted orientation subsequent to its use and the tubular needle retracted simultaneously within the barrel body of the syringe apparatus.

The plunger 16 is formed with a lower and upper annular seal 20 and 21, and a plunger head 25 that includes a coil spring 26 mounted to the needle chamber 13, whereupon retraction of the plunger to a second position, in a manner as illustrated in FIG. 6, extends the spring 26, as illustrated in FIG. 4, to effect removal of the ribbed projections 15 from the annular ribbed recess 29 and biases the needle chamber 13 interiorly of the cylindrical barrel 11 to simultaneously draw the associated needle member 14 therealong preventing reuse of the syringe apparatus.

Further it should be noted that either one or both of the upper and lower locking skirts 19 and 22 are formed of a semirigid material to permit cooperation of the confronting conical surfaces of each locking skirt to engage and deflect permitting the lower skirt 22 to be directed rearwardly beyond and past the upper skirt 19 into the orientation, as illustrated in FIG. 6.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A safety syringe apparatus comprising, an elongate cylindrical barrel, the barrel including a lower skirt and including a needle body defined by a second diameter lesser than a first diameter defined by the cylindrical barrel, the cylindrical barrel including an opened upper end receiving a plunger within the cylindrical barrel to permit reciprocation of the plunger relative to the barrel, and the needle body defining a needle chamber mounted within the needle body, the needle chamber including a tubular needle coaxially mounted to the needle chamber and the needle member arranged in fluid communication with an interior cavity of the cylindrical barrel through the needle chamber, wherein the cavity is defined between a plunger head mounted to a forward terminal end of the plunger and the needle body, and an upper locking skirt integrally mounted to an interior surface of the barrel adjacent the upper terminal end of the barrel, and a lower locking skirt mounted to the plunger positioned below the upper locking skirt in a first position and displaced above the upper annular locking skirt to a second position between the upper annular locking skirt and the upper terminal end of the barrel, and wherein the lower annular locking skirt includes a lower annular edge, and the lower annular edge spaced about the plunger, including a lower conical surface directed upwardly toward the upper terminal end of the cylindrical barrel, and the upper annular locking skirt including an upper annular edge, and an upper conical surface directed downwardly towards the needle body, and the lower annular locking skirt defining a lower planar surface, and the upper locking skirt including an upper planar surface, the lower planar surface and the upper planar surface arranged in confronting relationship in the second position, and wherein the plunger head includes a coil spring fixedly mounted to the plunger head at an upper terminal end of the coil spring and fixedly mounted to the needle chamber at a lower terminal end of the coil spring to effect retraction of the needle chamber when the plunger is in the second position.

2. An apparatus as set forth in claim 1 wherein the needle chamber includes at least one ribbed projection, and the needle body includes an annular ribbed recess to receive the rear projection to secure the needle chamber within the needle body in the first position and permit release of the needle chamber relative to the needle body in the second position of the plunger relative to the barrel.

3. An apparatus as set forth in claim 2 including indicia mounted on the plunger above the lower annular skirt, wherein the indicia project above the upper terminal end of the barrel when the plunger is in the second position.

4. An apparatus as set forth in claim 3 wherein the lower annular locking skirt is formed of a semi-deformable material.

* * * * *